(12) United States Patent
Peemans et al.

(10) Patent No.: US 6,203,612 B1
(45) Date of Patent: Mar. 20, 2001

(54) PROCESS FOR CLEANING BISPHENOL CRYSTALLIZER

(75) Inventors: Rudy Peemans, Erps-Kwerps (BE); Jan Huibert Weijland, Roosendaal (NL); Mourice Van Sintemaartensdijk, Erps-Kwerps (BE)

(73) Assignee: General Electric Company, Pittsfield, MA (US)

( * ) Notice: Subject to any disclaimer, the term of this patent is extended or adjusted under 35 U.S.C. 154(b) by 0 days.

(21) Appl. No.: 09/539,131

(22) Filed: Mar. 30, 2000

(51) Int. Cl.$^7$ .............................. C07C 39/16; C07C 37/84
(52) U.S. Cl. .................. 117/68; 117/73; 117/78; 117/925; 117/927; 568/724; 568/727; 568/728; 23/295 R
(58) Field of Search .................. 117/68, 73, 78, 117/925, 927; 568/724, 727, 728; 23/295 R

(56) References Cited

U.S. PATENT DOCUMENTS

| | | |
|---|---|---|
| 4,107,218 | 8/1978 | Konrad et al. . |
| 4,294,994 | 10/1981 | Li . |
| 5,210,329 | 5/1993 | Gomes De Matos et al. . |
| 5,243,093 | 9/1993 | Kissinger et al. . |
| 5,245,088 | 9/1993 | Fimuro et al. . |
| 5,288,926 | 2/1994 | Patrascu et al. . |
| 5,368,827 | 11/1994 | Moriya et al. . |
| 5,786,522 | 7/1998 | Cipullo . |
| 5,856,589 | 1/1999 | Cipullo . |
| 5,874,644 | 2/1999 | Gammill . |

FOREIGN PATENT DOCUMENTS

718267 * 6/1996 (EP) .

* cited by examiner

Primary Examiner—Robert Kunemund
(74) Attorney, Agent, or Firm—Oppedahl & Larson LLP

(57) ABSTRACT

An alternative and improved method for cleaning cooling and/or crystallization surfaces of a crystallizer fouled with a crystallized bisphenol as a result of processing a slurry derived from the production of bisphenol is provided. The method includes the steps of:

(a) draining from 20 to 80%, and preferably about 50% of the slurry from the crystallizer;

(b) replacing the drained slurry with a solvent comprising phenol, thereby forming a diluted slurry;

(c) increasing the temperature in the crystallizer to a temperature at which the crystallized bisphenol is dissolved in the diluted slurry, and then rapidly cooling the diluted slurry to a temperature of 45 to 55° C.; and (d) adding a seed slurry containing solid bisphenol at a concentration of 5 to 30%. The seed slurry has a temperature of 45 to 55° C. and is added until conditions are established at which bisphenol crystals added to the crystallizer do not redissolve.

10 Claims, 2 Drawing Sheets

SLURRY FEED FROM B CRYSTALLIZER TO A CRYSTALLIZER AND VICE VERSA

PROCESS FOR CLEANING BISPHENOL CRYSTALLIZER

FIELD OF THE INVENTION

This application relates to a process for cleaning a crystallizer used in the recovery of bisphenols, such as bisphenol A.

BACKGROUND OF THE INVENTION

Bisphenols, and in particular bisphenol A (2,2 bis(p-hydroxyphenyl) propane), have become industrially significant reactants for a number of processes including the preparation of polycarbonates. Bisphenols are prepared on an industrial scale by one of two processes: an acid-catalyzed or HCl process and an ion exchange process, in which an acidic ion exchange resin such as sulfonic acid-substituted polystyrene is employed.

The bisphenol is prepared by condensation of two moles of phenol with one mole of a ketone or aldehyde, for example acetone, in the presence of an acidic catalyst. In addition to the bisphenol, however, the product stream from the reaction includes unreacted phenol, which is included in excess over the stoichiometric requirement, and various isomers of the desired bisphenol and other by-products. Because these by-products can compromise the properties of products made using the bisphenol, they need to be separated. One technique for accomplishing this separation involves cooling the product stream to induce crystallization of a 1:1 bisphenol:phenol adduct which can then be further processed by washing, distillation, extraction and/or steam stripping to produce a purified bisphenol product. Processes for the production and purification of bisphenols are well known, and are described inter alia in U.S. Pat. Nos. 4,107,218; 4,294,994; 5,210,329; 5,243,093; 5,245,088; 5,288,926; 5,368,827; 5,786,522; and 5,874,644.

The crystallization of bisphenol from the reactant stream is generally carried out in a crystallizer which is designed for continuous or semi-continuous operation. The crystallization coolers have a complex interior structure to provide significant surface area for heat exchange between the bisphenol reaction stream and a circulating coolant. Over time, adduct precipitates out on the cooling surfaces on the interior crystallizer, reducing the efficiency of cooling and in some cases plugging orifices in the crystallizer and restricting flow of materials into and out of the crystallizer. When this happens, the crystallizer must be taken off-line for a period of time for cleaning. This interruption of the manufacturing process is costly, and it is therefore desirable to perform the cleaning as infrequently as possible, and with maximum effectiveness.

One method for cleaning the crystallizer and associated coolers is by increasing the temperature on the inside of the crystallizer to melt out deposits of crystals that may have formed. This can be accomplished by increasing the temperature of the heat exchange fluid, or by introducing hot phenol into the interior of the crystallizer. This method, however, is not always effective, and generally requires about 24 hours of down time to complete the cleaning procedure. In addition, this type of process suffers from poor reproducibility, and requires delicate control of the start-up procedure to return the crystallizer to the efficient production of the desired crystallized bisphenol adduct. U.S. Pat. No. 5,856,589 discloses an alternative approach in which phenol containing from 3 to 40 weight percent of water is used to dissolve deposited bisphenol adduct from the cooling and crystallization surfaces. The use of combinations of phenol and water reduces the time required for a melt out and the frequency of required melt outs. Nevertheless, there remains a need for further improvements in cleaning procedures, to further reduce the process down-time associated with such cleaning.

SUMMARY OF THE INVENTION

The present invention provides an alternative and improved method for cleaning cooling and/or crystallization surfaces of a crystallizer fouled with a crystallized bisphenol as a result of processing a slurry derived from the production of bisphenol. The method comprises the steps of:

(a) draining from 20 to 80%, and preferably about 50% of the slurry from the crystallizer;

(b) replacing the drained slurry with a solvent comprising phenol, thereby forming a diluted slurry;

(c) increasing the temperature in the crystallizer to a temperature at which the crystallized bisphenol is dissolved in the diluted slurry, and then rapidly cooling the diluted slurry to a temperature of 45 to 55° C.; and (d) adding a seed slurry containing solid bisphenol at a concentration of 5 to 30%, said seed slurry having a temperature of 45 to 55° C., until conditions are established at which bisphenol crystals added to the crystallizer do not redissolve.

DETAILED DESCRIPTION OF THE INVENTION

Figure 1:
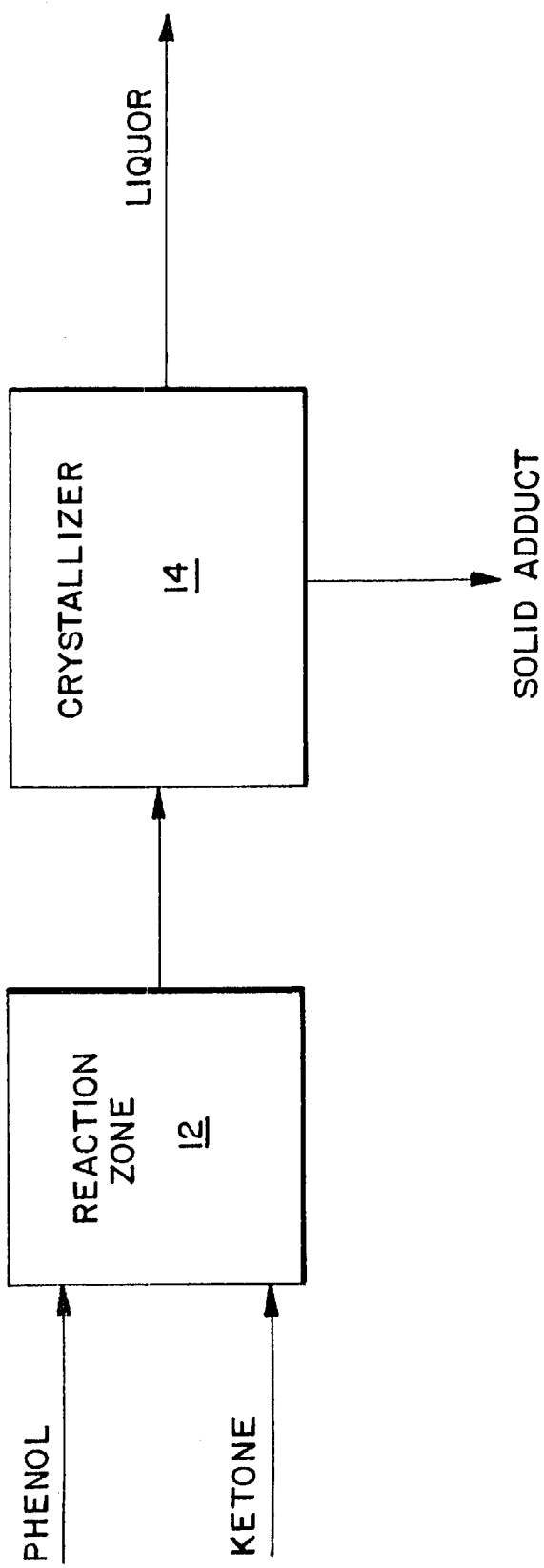
FIG. 1 shows a schematic representation of a plant for the manufacture of bisphenol A.

FIG. 1 shows a schematic representation of a plant for the manufacture of bisphenol A. As shown, phenol and a ketone such as acetone are introduced into a reaction zone 12 where the condensation to bisphenol occurs. Preferably, the reaction zone contains an acidic ion exchange resin such as sulfonated polystyrene, cross linked with divinyl benzene to catalyze the condensation reaction. The product of this reaction stream is introduced into a crystallizer 14 from which a solid adduct stream and a liquor are recovered.

Figure 2:
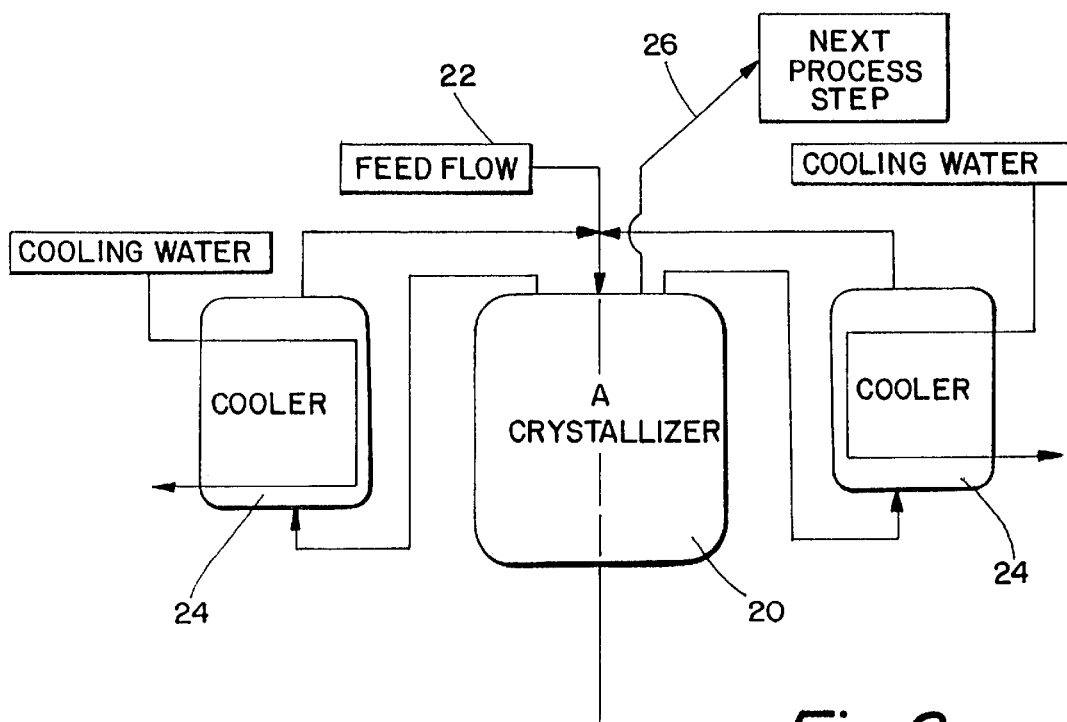
FIG. 2 shows the structure of an embodiment of a crystallizer useful in the method of the invention in more detail.
Figure 2:
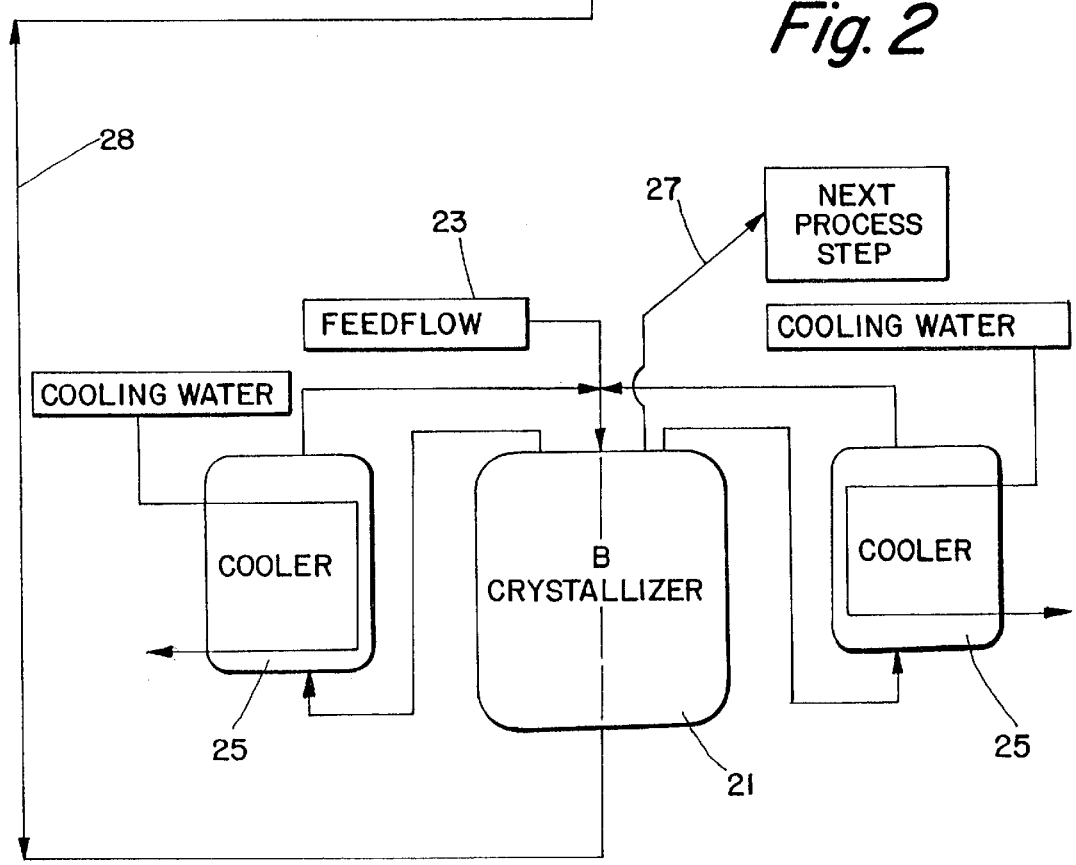

FIG. 2 shows the structure of an embodiment of crystallizer 14 in more detail. In the embodiment shown in FIG. 2, two crystallizers 20, 21, are operated in parallel in normal operation. Thus, a separate feed flow 22, 23 is provided to each of the crystallizers. The contents of the crystallizers 20, 21 are passed through coolers 24, 25 and product is recovered from each crystallizer via product recovery lines 26, 27.

In accordance with the method of the present invention, the crystallizer 14 is periodically treated to reduce build-up of adduct bisphenol on the crystallizer surfaces. In this process, the crystallizer 14 is partially emptied by draining from 20 to 80%, and preferably about 50% of the slurry from the crystallizer; and replacing the drained slurry with a solvent comprising phenol, thereby forming a diluted slurry. The solvent may in addition contain water, and/or acetone, bisphenol A (BPA) or BPA-type impurities if desired. The temperature inside the crystallizer is first increased to a level at which the crystallized bisphenol is dissolved in the diluted slurry, and then rapidly reduced to cool the diluted slurry to a temperature of 45 to 55° C. A seed slurry containing bisphenol crystals at a temperature of 45 to 55° C. is then added until conditions are established at which bisphenol crystals added to the crystallizer do not redissolve.

The cleaning procedure of the invention offers several advantages over alternative procedures known in the art. First, the method of the invention is rapid, allowing cleaning of a large scale crystallizer (throughput of 59 metric tons/hour) in a period of 6–8 hours. This time is broken down as follows:

(1) draining part of the slurry and replacing with phenol to increase the solubility of bisphenol—elapsed time: about 0.5–4 hours (2) heating the system to a temperature of 70° C. to dissolve the bisphenol crystals in the crystallizer—elapsed time: about 15–30 minutes (3) rapidly cooling the system to a temperature of 45 to 55° C.—elapsed time: about 15 minutes to 1 hour (4) feeding a high concentration of cold (45–55° C.) bisphenol slurry (seed crystals)—elapsed time to reestablish crystallization conditions: about 15 minutes to 1 hour.

The cooling process is preferably complete, or at least substantially complete prior to the addition of the seed crystals. It will, of course be appreciated that some additional temperature adjustment may occur as a result of the addition of the seed crystals, but this should be only fine-tuning to achieve the exact temperature desired for resumption of normal operation. Thus, the temperature of the slurry after the cooling step will generally by within 1–5 degrees C. of the temperature of the seed crystal slurry to be added.

A significant portion of the reduction in the amount of time required for the process of the invention results from reducing the time required for cooling the crystallizer containing the dissolved bisphenol. This reduction is possible because of the reduced concentration of bisphenol in the solution which results from the replacement of a portion of the slurry with a solvent for bisphenol, i.e., phenol. In one embodiment of the invention, the amount of slurry is reduced by about 50% when the concentration of bisphenol in the crystallizer is about 20–30% and replaced with phenol. If the total concentration of bisphenol is lower, than a lesser portion of the volume can be replaced, while if the concentration of bisphenol is higher, or if substantial amounts of bisphenol have accumulated on the crystallizer surfaces, a larger portion, up to about 80% may be replaced.

The cooling of the diluted bisphenol solution is carried out "rapidly." It will be appreciated that the actual amount of time required for this cooling will depend on various parameters including the volume of the crystallizer and the efficiency of the heat exchangers employed. Thus, it is not possible to quantify the term rapidly in isolation from the specific apparatus employed. However, as used herein, "rapid" cooling results when the heated circulating fluid (~70° C.) is replaced with a circulating fluid having a temperature within the target range of 45–55° C. without intermediate temperature steps which would make the cooling more gradual.

The solvent with which the removed slurry is replaced is one which contains phenol. The solvent may be all phenol, or it may contain various added materials, including water as described in a related but different process in U.S. Pat. No. 5,856,589, or other cosolvents such as acetone which may facilitate solubilization of bisphenol without interfering with the later crystallization processes.

Once the diluted bisphenol solution has been cooled, a slurry of bisphenol seed crystals is added to reestablish conditions suitable for crystallization. The drained liquid removed from the crystallizer can be used for this purpose. When sufficient bisphenol has been added in this way to reach a temperature of 44–55° C. and concentration where new crystals added to the crystallizer do not redissolve, the crystallizer can be brought back on line for normal operation. Although the crystallizer has already been cooled to about this same temperature, the temperature of the added seed crystal slurry plays an important role in establishing the actual final temperature and ensuring the proper conditions exist for resumption of normal crystallization.

The present invention offers several benefits which increase process efficiency and extend equipment lifetimes. Because the first crystals are produced in the presence of seed crystals and the cooling is done partially by introducing a cold bisphenol slurry, crystal formation on the surface of the coolers is reduced. No scaling of the cooler surfaces after the clean-out procedure is therefore necessary, and this increases the lifetime of the crystallizer. Furthermore, using the process of the invention, all of the crystallizer surfaces, i.e, body, pipes, pumps and coolers) get cleaned as opposed to only the coolers. This too increases the lifetime of the crystallizer.

As shown in FIG. 2, one embodiment of the present invention makes use of two crystallizers, operated in parallel. In practice, using such an apparatus, one could reduce the line throughput by 50% during cleaning operations, with the two crystallizers being taken off-line alternately for cleaning periods. When operating in this mode, it is advantageous to have an interconnecting line 28 joining the two crystallizers 20, 21. This allows (1) the product removed from one crystallizer to be transferred into the other crystallizer for continued processing and (2) the transfer of crystals from one crystallizer as the seed crystals for the other at the end of the cleaning cycle. Alternatively, if the crystallizers of FIG. 2 were highly fouled, cleaning of both at the same time might be required. Further, it will be appreciated that a system with a single crystallizer, or with more than two crystallizers operating in parallel might be employed to achieve cost-effective operation, depending on the size of the crystallizer and the throughput of the associated plant.

The invention will now be further described by way of the following non-limiting example.

EXAMPLE

In a specific example of the method of the invention, a 80–85 m³ crystallizer system (vessel volume 60 m³) used in the production of bisphenol A is cleaned. The lines which are to be used in the cleanout procedure are steamed to heat the lines and remove any residual material. The feed flow from the bisphenol A line to the crystallizer is then stopped, and the draining procedure started. The crystallizer is drained in two phases. First the coolers are drained, and immediately refilled with recycled phenol. Then the body of the crystallizer is drained to remove a total of about 40 m³ (50% of total volume) of the bisphenol A slurry. The complete drain time for the crystallizer body requires about 1 hour. The crystallizer body is then refilled with fresh or recycled phenol over a period of about 2.5 hours. The refilled crystallizer is heated using steam circulating in the shells. An internal temperature of 70° C. is reached within about 15 minutes. The steam in the cooling water circulation loop is then replaced with hot condensate, and the internal temperature is maintained at 70° to completely dissolve the bisphenol A in the crystallizer. This is generally achieved with a circulation time of at least 15 minutes for the charged phenol, and/or by achieving a minimum temperature of 70°

C. Preferably, both conditions are met. Next, the cooling water is changed to a stream having a temperature of 47° C. to lower the temperature of the material in the crystallizer to 51° C. in a period of 30 minutes. The use of colder cooling water can give rise to scaling, and thus is not recommended. A seed crystal slurry in then added to cooled crystallizer, and material is removed from the crystallizer via a rotary vacuum filter (RVF). The inflow of seed crystals is continued until crystals are detected in the RVF, at which time normal flow the crystallizer is resumed.

What is claimed is:

1. A method for cleaning a cooling or crystallization surface surface of a crystallizer fouled with a crystallized bisphenol, said crystallizer containing a slurry derived from the production of bisphenol, comprising the steps of:

(a) draining from 20 to 80% of the slurry from the crystallizer;

(b) replacing the drained slurry stream with a solvent comprising phenol, thereby forming a diluted slurry;

(c) increasing the temperature in the crystallizer to a temperature at which the crystallized bisphenol is dissolved in the diluted slurry, and then rapidly cooling the diluted slurry to a temperature of 45 to 55° C.; and (d) adding a seed slurry containing solid bisphenol at a concentration of at least 5%, said seed slurry having a temperature of 45 to 55° C., until conditions are established at which bisphenol crystals added to the crystallizer do not redissolve.

2. The method of claim 1, wherein about 50% of the slurry is drained from the crystallizer.

3. The method of claim 1, wherein the bisphenol is bisphenol A.

4. The method of claim 3, wherein about 50% of the slurry is drained from the crystallizer.

5. In a method for producing a bisphenol comprising the steps of reacting a first reactant stream containing phenol and a second reactant stream containing a ketone or aldehyde to produce a product mixture containing the bisphenol; feeding the product mixture as a slurry to a crystallizer to produce crystals of a 1:1 bisphenol:phenol adduct; and recovering the adduct, the improvement comprising periodically cleaning the crystallizer using a method comprising the steps of:

(a) draining from 20 to 80% of the slurry from the crystallizer;

(b) replacing the drained slurry stream with a solvent comprising phenol, thereby forming a diluted slurry;

(c) increasing the temperature in the crystallizer to a temperature at which the crystallized bisphenol is dissolved in the diluted slurry, and then rapidly cooling the diluted slurry to a temperature of 45 to 55° C.; and (d) adding a seed slurry containing solid bisphenol at a concentration of at least 5%, said seed slurry having a temperature of 45 to 55° C., until conditions are established at which bisphenol crystals added to the crystallizer do not redissolve.

6. The method of claim 5, wherein about 50% of the slurry is drained from the crystallizer.

7. The method of claim 5, wherein the bisphenol is bisphenol A.

8. The method of claim 7, wherein about 50% of the slurry is drained from the crystallizer.

9. The method of claim 5, wherein the product mixture is fed to two or more crystallizers operated in parallel, and wherein the two or more crystallizers are taken off line for cleaning at different times.

10. The method of claim 9, wherein the crystallizers are connected to one another, and wherein slurry is transferred from one crystallizer to another to serve as the seed slurry of step (d).

* * * * *